US012577187B2

(12) United States Patent
Gabelle et al.

(10) Patent No.: US 12,577,187 B2
(45) Date of Patent: Mar. 17, 2026

(54) PROCESS FOR THE DEHYDROGENATION OF ETHANOL IN A MULTITUBULAR REACTOR

(71) Applicants: IFP Energies nouvelles, Rueil-Malmaison (FR); COMPAGNIE GENERALE DES ETABLISSEMENTS MICHELIN, Clermont-Ferrand (FR)

(72) Inventors: Jean-Christophe Gabelle, Rueil-Malmaison (FR); Vincent Coupard, Rueil-Malmaison (FR); Rejane Dastillung, Rueil-Malmaison (FR); Mickael Mejean, Rueil-Malmaison (FR)

(73) Assignees: IFP Energies nouvelles, Rueil-Malmaison Cedex (FR); COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 512 days.

(21) Appl. No.: 18/028,280

(22) PCT Filed: Sep. 13, 2021

(86) PCT No.: PCT/EP2021/075135
§ 371 (c)(1),
(2) Date: Mar. 24, 2023

(87) PCT Pub. No.: WO2022/063620
PCT Pub. Date: Mar. 31, 2022

(65) Prior Publication Data
US 2023/0373892 A1      Nov. 23, 2023

(30) Foreign Application Priority Data
Sep. 25, 2020      (FR) ...................................... 2009759

(51) Int. Cl.
*C07C 45/00* (2006.01)
*C07C 1/207* (2006.01)
*C07C 7/00* (2006.01)

(52) U.S. Cl.
CPC .......... *C07C 45/002* (2013.01); *C07C 1/2076* (2013.01); *C07C 7/005* (2013.01)

(58) Field of Classification Search
CPC ...... C07C 45/002; C07C 1/2076; C07C 7/005
See application file for complete search history.

(56) References Cited

U.S. PATENT DOCUMENTS

| | | | |
|---|---|---|---|
| 5,227,563 | A | 7/1993 | Fukuhara et al. |
| 10,358,396 | B2 | 7/2019 | Dastillung et al. |
| 11,358,911 | B2 | 6/2022 | Drobyshev et al. |
| 11,584,698 | B2 | 2/2023 | Nesterenko et al. |
| 2022/0048833 | A1 | 2/2022 | Drobyshev et al. |

FOREIGN PATENT DOCUMENTS

FR      3090632 A1      6/2020

OTHER PUBLICATIONS

International search report PCT/EP2021/075135 dated Nov. 22, 2021 (pp. 1-2).
Filho R.Maciel et al: "A multitubular reactor for obtention of acetaldehyde by oxidation of ethyl alcohol", Chemical Engineering Science, vol. 47, No. 9-11, Jun. 1, 1992 (Jun. 1, 1992), GB, pp. 2571-2576, XP055810653, ISSN: 0009-2509, DOI: 10.1016/0009-2509(92)87095-8.

*Primary Examiner* — Sikarl A Witherspoon
(74) *Attorney, Agent, or Firm* — Millen, White, Zelano & Branigan, P.C.; Brion P. Heaney

(57) ABSTRACT

The invention relates to a process for the dehydrogenation of a feedstock comprising ethanol, using at least one multitubular reactor advantageously comprising a plurality of tubes comprising at least one dehydrogenation catalyst, and a calender, said feedstock being introduced into the tubes in gas form, at an inlet temperature of greater than or equal to 240° C., a pressure between 0.1 and 1.0 MPa, and a WWH between 2 and 15 $h^{-1}$, wherein a heat-transfer fluid circulates in said calender at a flow rate such that the weight ratio of said heat-transfer fluid relative to said feedstock is greater than or equal to 1.0, and such that said heat-transfer fluid is introduced into said calender in gas form at an inlet temperature of greater than or equal to 260° C. and at an inlet pressure of greater than or equal to 0.10 MPa, and less than or equal to 1.10 MPa, and leaves the calender at least partly in liquid form.

27 Claims, No Drawings

PROCESS FOR THE DEHYDROGENATION OF ETHANOL IN A MULTITUBULAR REACTOR

FIELD OF THE INVENTION

The present invention relates to a process for the catalytic dehydrogenation of ethanol, in particular employing at least one multitubular reactor having condensation of a heat-transfer fluid. The present invention also relates to a process for the production of butadiene from ethanol which comprises, as first reaction stage, the process for the catalytic dehydrogenation of ethanol in a multitubular reactor having condensation of the heat-transfer fluid to produce acetaldehyde, followed by a second reaction stage producing butadiene from a mixture of ethanol and acetaldehyde.

PRIOR ART

The reaction for the dehydrogenation of ethanol to give acetaldehyde can be a first reaction stage in several processes, such as, for example, in a process for the conversion of ethanol into butadiene, known in particular under the name of the Ostromislensky process and associated with the Lebedev process. The ethanol dehydrogenation reaction is an equilibrium reaction which exhibits degrees of conversion of the ethanol conventionally in the vicinity of 30%. It is a highly endothermic reaction (AH reaction=72.4 kJ/mol). A reactor technology making possible appropriate thermal compensation is thus necessary.

More generally, there exist several technologies for industrial dehydrogenation processes: the Catofin® process of ABB, the Oleflex™ process of UOP, the Star Process® process of ThyssenKrupp and the PDH process of Linde. All these industrial processes have the objective of the dehydrogenation of light alkanes to give olefins, in particular the dehydrogenation of propane and butane to give propylene and butene respectively. More specifically, the Catofin® and Oleflex™ processes employ batteries of adiabatic reactors in parallel, respectively having fixed catalytic beds and having moving catalytic beds. The PDH process, for its part, uses reactors having fixed beds heated externally by a fuel. The Star Process® process carries out the reaction in tubes placed in a furnace on a feedstock diluted with steam. It appears that the choice of the reactor technology depends, at least in part, on the catalyst used for the dehydrogenation of the alkanes carried out.

Multitubular reactors, also called reactor-exchangers, can be used to make it possible for processes to operate under isothermal or pseudoisothermal conditions. This is the case, for example, with the process of the dehydration of isopropanol described in the patent U.S. Pat. No. 5,227,563 of Mitsui Petrochemical. In this patent, isopropanol is dehydrated to give propylene in the presence of alumina, between 290° C. and 320° C. in a vertical tubular reactor, with a length of 0.5 m and an internal diameter of 25.4 mm, to obtain degrees of conversion of the isopropanol of at least 85% and a selectivity for propylene of 79% or more.

The patent application WO 2018/046515 for its part describes a process for the dehydration of isobutanol to give butene comprising a stage of simultaneous dehydration and isomerization, carried out under isothermal or pseudoisothermal conditions at a temperature of 300° C. or 350° C., in the presence of a catalyst comprising an FER zeolite, in a multitubular reactor. The degrees of conversion of the isobutanol which are obtained by this process are of the order of 100%, with a selectivity for butenes of at least 97%.

Finally, the application FR 3 089 973 describes a process for the dehydration of ethanol to give ethylene, in a multitubular reactor, in the presence of ZSM-5 zeolite and at an inlet temperature of the feedstock in the tubes of between 420 and 430° C. In order to maintain the temperature, salts molten at 470° C. are used as heat-transfer fluid. Under these conditions, the degrees of conversion of ethanol which are achieved are greater than 99% with a selectivity for ethylene of at least 98%.

However, none of these documents addresses the reaction for the dehydrogenation of ethanol to give acetaldehyde. It is thus an objective of the invention to provide a process for the dehydrogenation of ethanol to give acetaldehyde, making it possible to achieve a satisfactory conversion of the ethanol and a satisfactory selectivity for acetaldehyde, while avoiding premature deactivation of the catalyst and while limiting high consumption of utilities, such as steam, and while minimizing the capital and operating costs.

SUMMARY OF THE INVENTION

The invention relates to a process for the dehydrogenation of ethanol to give acetaldehyde, comprising a stage of dehydrogenation of a feedstock comprising ethanol, said dehydrogenation stage employing a reaction section comprising at least one multitubular reactor which comprises one or a plurality of tubes and a shell, said tube(s) each comprising at least one fixed bed of at least one dehydrogenation catalyst, said feedstock feeding said tube(s) in gaseous form, at an inlet temperature of said feedstock of greater than or equal to 240° C., at an inlet pressure of said feedstock of between 0.1 and 1.0 MPa, and at a weight hourly space velocity (WWH) of the feedstock at the inlet of between 2 and 15 h⁻¹, a heat-transfer fluid circulating in said shell so that said heat-transfer fluid is introduced into said shell in gaseous form and is, at the shell outlet, at least partly in liquid form, said heat-transfer fluid being introduced into the shell at a flow rate such that the ratio of the flow rate by weight of said heat-transfer fluid at the shell inlet, with respect to the flow rate by weight of said feedstock at the inlet of the tube(s), is greater than or equal to 1.0, said heat-transfer fluid being introduced into the shell at an inlet temperature of the heat-transfer fluid of greater than or equal to 260° C. and less than or equal to 400° C., and at an inlet pressure of the heat-transfer fluid of greater than or equal to 0.10 MPa and less than or equal to 1.10 MPa;

said process producing a dehydrogenation effluent comprising at least acetaldehyde, hydrogen and unconverted ethanol.

The present invention exhibits the advantage of compensating for the endothermicity of the ethanol dehydrogenation reaction (ΔH reaction=72.4 kJ/mol) by maintaining the temperature of the reaction medium in a range of temperatures which are suitable for the dehydrogenation reaction, in particular at a value of greater than or equal to 230° C., preferably of greater than or equal to 240° C., in a preferred way of greater than or equal to 250° C. The present invention employs a reactor of reactor-exchanger type and according to a particular form of condensation of the heat-transfer fluid. The phase-change enthalpy of the heat-transfer fluid can thus be used to provide the heat necessary for the energy requirements of the ethanol dehydrogenation reaction. The present invention also makes it possible to have a homogeneous temperature on the exterior wall of the tubes inside which the reaction is carried out.

The present invention thus makes it possible to achieve satisfactory degrees of conversion of the ethanol and a high selectivity for acetaldehyde, in particular degrees of conversion of the ethanol of greater than or equal to 25%, preferably of the order of 35%, and a selectivity for acetaldehyde of greater than 90%.

Another advantage of the invention lies in the fact that the thermal compensation is obtained without addition to the feedstock of a diluent which appears necessary, in particular when adiabatic reactors are used, to "thermally buffer" the temperature drop induced by the endothermicity of the reaction by transmitting its sensible heat to the reaction. The diluent conventionally used as "thermal buffer" is steam. In point of fact, too high a water content in the reactor, for example a water content of greater than 20% by weight, with respect to the total weight of the feedstock, can be detrimental to the dehydrogenation catalyst and cause its early deactivation. Thus, the ethanol dehydrogenation process of the present invention requires no addition of diluent and so makes it possible to limit the risk of early deactivation of the dehydrogenation catalyst.

The present invention also offers the advantage of being able to dehydrogenate ethanol feedstocks of very diverse compositions and origins, for example which can comprise water as a mixture with ethanol. This is because the present invention in particular can apply to ethanol feedstocks produced from renewable sources resulting from biomass, often called "bioethanol". It can also apply to an ethanol-rich effluent, for example obtained after treatment of a reaction effluent resulting in particular from the conversion of ethanol into butadiene and advantageously recycled to the reaction section, said reaction section comprising in particular a stage of dehydrogenation of ethanol as described in the patent FR 3 026 100. More particularly, the present invention makes possible the dehydrogenation of the ethanol-rich effluent obtained in stage E1) of the patent FR 3 026 100 and which can comprise, for example, up to 18% by weight of water.

Furthermore, the fact of avoiding the addition of a diluent to the feedstock advantageously makes it possible to limit the size of the items of equipment and the number of subsequent separation stages and consequently to minimize the capital and operating costs of the process, in particular with respect to an ethanol dehydrogenation process requiring dilution with steam.

The present invention exhibits yet another advantage: that of avoiding the multiplication of the number of catalytic beds necessary. This is because, with the technology of adiabatic reactors, a sequence of fixed beds of catalysts, intercalated with heat exchangers, is necessary to compensate for the endothermicity of the reaction and to achieve an ethanol conversion of the order of 30%. On the contrary, the present invention, which proposes to use a multitubular reactor coupled to the particular form of condensation of a suitable heat-transfer fluid, makes it possible to achieve the targeted degrees of conversion (between 25% and 35%, indeed even between 30% and 35%) and a high selectivity for acetaldehyde (greater than or equal to 90%), while limiting the capital and operating costs of the process.

DESCRIPTION OF FORMS OF THE INVENTION

According to the present invention, the expressions "of between . . . and . . . " and "between . . . and . . . " are equivalent and mean that the limiting values of the interval are included in the described range of values.

If such were not the case and if the limiting values were not included in the described range, such a piece of information will be revealed by the present invention.

Within the meaning of the present invention, the various ranges of parameters for a given stage, such as the pressure ranges and the temperature ranges, can be used alone or in combination. For example, within the meaning of the present invention, a range of preferred pressure values can be combined with a range of more preferred temperature values.

Subsequently, particular and/or preferred embodiments of the invention may be described. They can be employed separately or combined together, without limitation of combination when this is technically feasible.

The invention thus relates to a process for the dehydrogenation of ethanol to give acetaldehyde, comprising, preferably consisting of, a stage of dehydrogenation of a feedstock comprising ethanol, preferably at least 50% by weight of ethanol, preferentially at least 70% by weight of ethanol, in a preferred way at least 80% by weight of ethanol, and optionally water, in which:

said dehydrogenation stage employs a reaction section comprising at least one multitubular reactor which comprises one or a plurality of tubes, preferably a plurality of tubes and a shell, said tube(s) being very advantageously made of steel of any type, preferably made of alloy steel and in a preferred way made of stainless steel, preferably having a length between 1.0 and 6.0 m, in a preferred way between 2.0 and 3.0 m, preferably an internal diameter between 30.0 and 60.0 mm, preferentially between 40.0 and 50.0 mm, and preferably a tube wall thickness between 1.5 and 5.0 mm, preferentially between 2.0 and 4.0 mm and in a preferred way between 2.2 and 3.2 mm, each tube comprises at least one fixed bed comprising at least one dehydrogenation catalyst, said dehydrogenation catalyst preferably comprising at least the element copper on an inorganic support, preferably silica, said catalyst very advantageously being in the form of particles with a mean equivalent diameter between 0.5 and 10.0 mm, preferably between 1.0 and 5.0 mm, said feedstock feeds said tube(s) in gaseous form, at an inlet temperature of said feedstock into the tube(s) of greater than or equal to 240° C., preferably between 240° C. and 350° C., preferentially between 250° C. and 300° C., in a preferred way between 260° C. and 290° C., at an inlet pressure of said feedstock into the tube(s) of between 0.1 and 1.0 MPa, preferably between 0.2 and 0.5 MPa, preferentially between 0.3 and 0.4 MPa, and at an hourly space velocity (WWH) of the feedstock at the inlet of the multitubular reactor of between 2 and 15 $h^{-1}$, preferably between 2 and 10 $h^{-1}$, a heat-transfer fluid circulates in said shell, preferably cocurrentwise to the feedstock in the tube(s), so that said heat-transfer fluid is introduced into said shell in gaseous form and is, at the shell outlet, at least partly in liquid form, said heat-transfer fluid is introduced into the shell of said multitubular reactor at a flow rate such that the ratio of the flow rate by weight of said heat-transfer fluid at the shell inlet, with respect to the flow rate by weight of said feedstock at the inlet of said tubes, is greater than or equal to 1.0, preferably greater than or equal to 1.5, and advantageously less than or equal to 10.0, preferably less than or equal to 5.0, in a preferred way less than or equal to 2.0, said heat-transfer fluid is introduced into the shell of said multitubular reactor at an inlet temperature of the heat-transfer fluid of greater than or equal to 260° C., preferably of greater than or equal to 270° C., in a preferred way of greater than or equal to 290° C., and of less than or equal to 400° C., preferably of less than or equal to 380° C., and at an inlet pressure of the heat-transfer fluid of greater than or equal to 0.10 MPa, preferably of greater than or equal to 0.13 MPa, in a preferred way of greater than or equal to 0.20 MPa, and of less than or equal to 1.10 MPa, in a preferred way of less than or equal to 0.85 MPa, said process producing a dehydrogenation effluent comprising at least acetaldehyde, hydrogen and unconverted ethanol.

Feedstock

In accordance with the invention, the feedstock treated in the dehydrogenation process is a feedstock comprising ethanol. Preferably, said feedstock comprises at least 50% by weight of ethanol, preferentially at least 70% by weight of ethanol, in a preferred way at least 80% by weight of ethanol.

The feedstock of the dehydrogenation process can in addition optionally comprise water, preferably at a content of less than 50% by weight, preferentially of less than 30% by weight, in a preferred way of less than 20% by weight, for example between 1% and 20% by weight, of water, with respect to the total weight of the feedstock.

The feedstock, in particular comprising less than 50% by weight of ethanol, can be concentrated, prior to the process of the invention, by any means known to a person skilled in the art, for example by distillation, by absorption, by pervaporation or by extraction with a solvent.

Said feedstock can comprise impurities, in addition to water, such as for example butanol, preferably at a content of less than or equal to 10% by weight, preferentially of less than or equal to 5% by weight, in a preferred way of less than or equal to 2% by weight, with respect to the total weight of said feedstock.

The feedstock treated in the process according to the invention is optionally obtained by a process for the synthesis of alcohol starting from fossil resources, such as, for example, starting from coal, natural gas or carbon-based waste.

Preferably, the feedstock advantageously originates from non-fossil resources. It can be obtained from renewable sources resulting from biomass, often called "bioethanol". Bioethanol is a feedstock produced biologically, preferably by fermentation of sugars resulting, for example, from sugar-producing plant crops, such as sugar cane (saccharose, glucose, fructose and sucrose), from beetroot, or also from starchy plants (starch) or from lignocellulosic biomass or from hydrolyzed cellulose (glucose (predominantly) and xylose, galactose), containing variable amounts of water. For a more complete description of the conventional fermentation processes, reference may be made to the publication "Les Biocarburants, État des lieux, perspectives et enjeux du développement [Biofuels, current state, perspectives and development challenges]", Daniel Ballerini, published by Technip, 2006.

Said feedstock can also advantageously be obtained from synthesis gas.

Said feedstock can also advantageously be obtained by hydrogenation of the corresponding acids or esters. In this case, acetic acid or acetic esters are advantageously hydrogenated using hydrogen to give ethanol. Acetic acid can advantageously be obtained by carbonylation of methanol or by fermentation of carbohydrates.

Said feedstock can also be an ethanol effluent, obtained after treatment (in particular after separation and purification stages) of an effluent resulting from a process for the conversion of ethanol into butadiene. More particularly, the feedstock of the dehydrogenation process can be an ethanol effluent predominantly comprising ethanol, that is to say comprising at least 50% by weight, preferably at least 70% by weight, preferentially at least 80% by weight, of ethanol, and obtained after treatment of a reaction effluent resulting from the conversion of ethanol into butadiene, said ethanol effluent advantageously being recycled to the reaction section which comprises in particular a stage of dehydrogenation of the ethanol. According to a very particular embodiment of the invention, the feedstock comprising ethanol is an ethanol-rich effluent, advantageously obtained on conclusion of a stage of treatment of the effluents from a process for the conversion of ethanol into butadiene, such as, for example, the ethanol-rich effluent advantageously obtained on conclusion of stage E1) of the process described in the patent FR 3 026 100. This ethanol-rich effluent can comprise in particular up to 18% by weight of water.

Dehydrogenation Stage

In accordance with the invention, the dehydrogenation process comprises at least a stage of dehydrogenation of said feedstock comprising ethanol, so as to produce a dehydrogenation effluent advantageously comprising at least acetaldehyde, hydrogen and conventionally unconverted ethanol. Said dehydrogenation effluent obtained can also comprise water, in particular when the feedstock itself comprises water. It can also comprise impurities, in particular already present in the feedstock, and/or co-products in particular generated during the dehydrogenation reaction.

Said dehydrogenation stage employs a reaction section comprising at least one multitubular reactor in which the dehydrogenation reaction takes place. The reaction section can comprise at least two multitubular reactors and preferably less than ten multitubular reactors. Preferably, the reaction section comprises two multitubular reactors, one being in operation, that is to say fed with feedstock and implementing the dehydrogenation reaction, the other being in regeneration-replacement mode. The expression "in regeneration-replacement mode" means that the multitubular reactor is not fed with feedstock comprising ethanol and that the catalyst is in the course of regeneration or of charging, or else is regenerated and/or charged and is ready to operate (that is to say, waiting for operation).

Advantageously, each multitubular reactor comprises one or a plurality of tubes and a shell. The dehydrogenation reaction advantageously takes place in the tube(s) of the multitubular reactor(s) advantageously in operation. In the continuation of the disclosure, the tube(s) of the multitubular reactor(s) can also be called reaction tube(s). The shell is the casing, typically cylindrical, of the reactor inside which the tube(s) are located, preferably parallel to one another and to the walls of the shell when there are several tubes, and in which a heat-transfer fluid circulates. The shell can also comprise one or more baffles or any other system, preferably distributed uniformly in the shell, in order to make possible good diffusion and homogenization of the heat-transfer fluid and thus good distribution of the heat. The shell and the tubes can have a particular design or a particular texture making it possible to promote the condensation and/or the discharge of the heat-transfer fluid.

According to the invention, each tube comprises at least one fixed bed comprising at least one dehydrogenation catalyst. Preferably, each tube contains a fixed bed of a dehydrogenation catalyst. Preferably, said dehydrogenation catalyst comprises at least the element copper, and optionally the element chromium, on an inorganic support, preferably silica. Very advantageously, the dehydrogenation catalyst is in the form of particles with a mean equivalent diameter between 0.5 and 10.0 mm, preferably between 1.0 and 5.0 mm. According to the invention, the mean equivalent diameter defines a mean equivalent diameter at the surface, advantageously determined by the laser diffraction method, and the mean equivalent diameter of the particles advantageously corresponds to the mean diameter of spheres having the same specific surface as said particles. For example, the dehydrogenation catalyst can be the Octolyst® 2001 or Octolyst® 2009 catalyst sold by Evonik.

Preferably, the multitubular reactor(s) comprise(s) a plurality of tubes in the shell, preferably at least 100 tubes, preferentially at least 1000 tubes, in a preferred way at least 2000 tubes. Generally, the multitubular reactors comprise up to 20 000 tubes, preferably up to 10 000 tubes. For example, each multitubular reactor can contain between 5000 and 6000 tubes.

Advantageously, the reaction tube(s) have a length preferably of between 1.0 and 6.0 m, in a preferred way between 2.0 and 3.0 m. When the multitubular reactor comprises a plurality of tubes, all the tubes of said multitubular reactor advantageously exhibit the same length, to within the accuracy due in particular to the manufacture and the machining of the tubes. The internal diameter of each reaction tube is preferably of between 30.0 and 60.0 mm, preferentially between 40.0 and 50.0 mm.

Advantageously, the reaction tube(s) exhibit(s) a wall thickness preferably between 1.5 and 5.0 mm, preferentially between 2.0 and 4.0 mm and in a preferred way between 2.2 and 3.2 mm. Thus, the nominal diameter, or external diameter, of a tube can vary between 33 and 70 mm, preferably between 44 and 56 mm. The specific dimensioning of the reaction tube(s), in particular the length, the internal diameter and the thickness of the wall, is advantageously adapted to the pressures exerted on the tube side (that is to say, inside the tube(s)) and on the shell side (that is to say, outside the tube(s)), while advantageously making it possible to limit the drops in pressures inside the tube(s) and thus to avoid the negative impact of the fall in pressure on the performance qualities of the dehydrogenation reaction, in particular to avoid a drop in the conversion of the ethanol.

The size of the multitubular reactor of the dehydrogenation stage c), such as the diameter of the shell, can be adapted by a person skilled in the art according to general knowledge, as a function in particular of the number of tubes, of their length and of their diameter.

Multitubular reactors, in particular industrial ones, and especially the tubes of said reactors, are conventionally made of a material which is inert with respect to the reaction, typically made of steel or nickel. The tube(s) of the multitubular reactor(s) in the dehydrogenation process is (are) preferably made of steel of any type, preferentially made of alloy steel and in a preferred way made of stainless steel. Very advantageously, the shell of the multitubular reactor(s), as well as any baffle optionally present in the shell, is in the same material as the reaction tubes, preferably made of steel of any type, preferentially made of alloy steel and in a preferred way made of stainless steel.

According to the invention, the feedstock is introduced in gaseous form into said tube(s) of each multitubular reactor advantageously in operation, preferably at one of the ends of said reaction tube(s) and in a preferred way simultaneously into all of the reaction tubes of the multitubular reactor when the latter contains a plurality of tubes. The feedstock feeds the reaction tube(s) at an inlet temperature of said feedstock of greater than or equal to 240° C., preferably of between 240° C. and 350° C., preferentially between 250° C. and 300° C., in a preferred way between 260° C. and 290° C., at an inlet pressure of said feedstock of between 0.1 and 1.0 MPa, preferably between 0.2 and 0.5 MPa, preferentially between 0.3 and 0.4 MPa, and at a weight hourly space velocity (WWH) of the feedstock at the inlet of the multitubular reactor of between 2 and 15 $h^{-1}$, preferably between 2 and 10 $h^{-1}$, in particular between 3 and 7 $h^{-1}$, for example 5 $h^{-1}$. Thus, the flow rate of the feedstock at the inlet of the multitubular reactor, which comprises, for example, between 4000 kg and 30 000 kg, preferably between 14 000 kg and 17 000 kg, of dehydrogenation catalyst, can vary between 20 000 and 150 000 kg/h, preferentially between 50 000 and 100 000 kg/h, in a preferred way between 70 000 and 85 000 kg/h. According to the invention, the weight hourly space velocity (WWH) can be defined as the ratio of the flow rate by weight of the total feedstock entering the multitubular reactor to the weight of dehydrogenation catalyst included in all of the reaction tubes of said multitubular reactor.

The inlet temperature of said feedstock into the multitubular reactor(s) can advantageously be gradually increased, while advantageously remaining in the range of inlet temperatures noted above, in order to compensate, at least in part, for the deactivation of the dehydrogenation catalyst.

The dehydrogenation stage of the process according to the invention can optionally employ a section for heating the feedstock, upstream of the reaction section. The heating of the feedstock in the optional heating section can be carried out by any method known to a person skilled in the art, for example by heat exchange with a fluid which can very particularly be the heat-transfer fluid circulating in the shell.

The flow of the feedstock can be in ascending or descending mode, preferably descending mode, in each tube.

According to the invention, a heat-transfer fluid circulates in the shell of the multitubular reactor(s) advantageously in operation, in particular between said reaction tubes, advantageously cocurrentwise with or countercurrentwise to, in a preferred way cocurrentwise with, the flow circulating inside the reaction tubes. The heat-transfer fluid is introduced into the shell of the multitubular reactor(s) in gaseous form and is, at the shell outlet, at least partly in liquid form (that is to say, in liquid form or as a gas-liquid mixture). In other words, the heat-transfer fluid is advantageously introduced into the shell in the form of saturated vapor (that is to say, in the vapor phase at the bubble point) and partly (or at least partly) condenses on contact with the tubes inside which the dehydrogenation reaction, which is an endothermic reaction, takes place. The contribution of heat necessary to maintain the temperature in the tube(s) in a range of temperatures compatible with the dehydrogenation reaction, in particular at least equal to 230° C., preferably greater than or equal to 240° C., very preferably greater than or equal to 250° C., is thus very advantageously ensured by the phase-change enthalpy, in particular the enthalpy of condensation, of the heat-transfer fluid used.

The heat-transfer fluid is chosen so as to be thermally stable under the operating conditions described above. The choice of the heat-transfer fluid can also be guided by other constraints: preferably, the heat-transfer fluid is inert with respect to the reactants and the products of the dehydrogenation reaction; preferably, the heat-transfer fluid does not induce corrosion of the items of equipment, such as the multitubular reactor or the ducts. Very advantageously, the heat-transfer fluid exhibits a single boiling point at a given pressure. It is in particular advantageously chosen so that it exhibits a boiling point or a range of saturated vapor temperatures (which depends on the vapor pressures) compatible with the dehydrogenation reaction and/or such that its enthalpy of change in phases from the gaseous state to the liquid state covers the energy requirement of the dehydrogenation reaction. Preferably, the heat-transfer fluid is an oil, preferably comprising a eutectic mixture of organic compounds, preferably of two organic compounds, very advantageously having close boiling points, preferably with saturated vapor pressures such that the difference between the saturated vapor pressures of the organic compounds of the oil, at a given temperature, is less than or equal to 50 Pa, preferably less than or equal to 20 Pa, in a preferred way less than or equal to 10 Pa. More particularly, the heat-transfer fluid comprises, preferably consists of, a mixture of biphenyl and of diphenyl oxide. For example, the heat-transfer fluid is the oil sold by Dow under the name DOWTHERM™ A.

Advantageously, the heat-transfer fluid is introduced into the shell of the multitubular reactor advantageously in operation at an inlet temperature of the heat-transfer fluid of greater than or equal to 260° C., preferably of greater than or equal to 270° C., in a preferred way of greater than or equal to 290° C., and of less than or equal to 400° C., preferably of less than or equal to 380° C., and at an inlet pressure of the heat-transfer fluid of greater than or equal to 0.10 MPa, preferably of greater than or equal to 0.13 MPa, in a preferred way of greater than or equal to 0.20 MPa, and of less than or equal to 1.10 MPa, preferably of less than or equal to 1.06 MPa and in a preferred way of less than or equal to 0.85 MPa. More particularly, the heat-transfer fluid is introduced into the shell advantageously in the form of saturated vapor, preferably at a temperature of greater than or equal to 260° C. and a pressure of greater than or equal to 0.10 MPa, preferably a temperature of greater than or equal to 270° C. and a pressure of greater than or equal to 0.13 MPa, preferably at a temperature of greater than or equal to 290° C. and a pressure of greater than or equal to 0.20 MPa, and preferably at a temperature of less than or equal to 400° C. and a pressure of less than or equal to 1.10 MPa, in a preferred way at a temperature of less than or equal to 380° C. and a pressure of less than or equal to 0.85 MPa.

The inlet temperature and/or pressure of the heat-transfer fluid in the shell can be gradually increased, advantageously in the inlet temperature and pressure ranges noted above, in order to compensate, at least in part, for the deactivation of the dehydrogenation catalyst.

The flow rate by weight of said heat-transfer fluid in the shell is advantageously adjusted so that the ratio of the flow rate by weight of said heat-transfer fluid in the shell, with respect to the flow rate by weight of the feedstock introduced into the tube(s), is greater than or equal to 1.0, preferably greater than or equal to 1.5, and advantageously less than or equal to 10.0, preferably less than or equal to 5.0, in a preferred way less than or equal to 2.0.

Under these conditions, and as the transfer coefficient on the shell side (that is to say, on the condensation side) is much greater than the transfer coefficient within the tubes, the temperature advantageously remains constant along each of the tubes of the reactor and equal to the condensation temperature of the heat-transfer fluid. The temperature is thus uniform for all the tubes and very close to the temperature of the shell, which is advantageous from a design of the reactor viewpoint since, the temperature being uniform throughout the reactor, the expansion of the material of the reactor will be the same between the tubes and between the tubes and the shell during operation, leading to a reduction in the cost of the item of equipment.

Advantageously, the dehydrogenation process can comprise a stage of conditioning of the heat-transfer fluid comprising a phase of recovery of the heat-transfer fluid at the shell outlet of the multitubular reactor of the dehydrogenation stage, followed by a phase of compression and/or heating of the heat-transfer fluid in order to obtain a heat-transfer fluid in gaseous form at the inlet temperature and pressure of the heat-transfer fluid in the shell of the dehydrogenation stage.

In such a reactor and with the particular operating conditions of the process according to the invention, in particular by using the enthalpy of condensation of the heat-transfer fluid introduced into the shell at specific temperatures and pressures and at a flow rate adjusted with respect to that of the feedstock in the reaction tubes, the reaction for the dehydrogenation of ethanol to give acetaldehyde advantageously takes place under isothermal or pseudoisothermal conditions, that is to say such that the temperature of the reaction medium at the reactor outlet (that is to say of the dehydrogenation effluent at the reactor outlet) is similar to the inlet temperature of the feedstock or exhibits a difference of less than 30° C., preferably of less than 15° C., with respect to the temperature of the feedstock at the reactor inlet.

Advantageously, under such conditions, the dehydrogenation effluent obtained on conclusion of the multitubular reactor advantageously in operation exhibits a temperature preferably of greater than or equal to 230° C., preferentially of greater than or equal to 240° C., in a preferred way of greater than or equal to 250° C. and in a preferred way of greater than or equal to 260° C., and preferably of less than or equal to 350° C., preferentially of less than or equal to 300° C., in a preferred way of less than or equal to 290° C., and a pressure at the reactor outlet of, for example, between 0.1 and 0.5 MPa and preferably between 0.2 and 0.4 MPa.

The specific conditions of the process according to the invention thus make it possible to achieve the desired performance qualities. In particular, the use of a reactor-exchanger under the specific operating conditions of the invention very advantageously makes it possible to obtain degrees of conversion of the ethanol of at least 25%, preferably of at least 30%, indeed even a conversion of the ethanol of 35%, and a high selectivity for acetaldehyde, in particular at least 90% by weight. And these performance qualities are achieved without addition of a thermal diluent, which might have harmful consequences with regard to the activity of the dehydrogenation catalyst, and without multiplying the number of catalytic beds and/or of reactors, as in a process comprising a sequence of adiabatic reactors, thus making it possible to limit the capital and operating costs. The method of contributing heat provided by the invention also makes it possible to easily adapt the operating conditions to the change in and the possible deactivation of the catalyst.

According to the invention, the conversion of the ethanol feedstock is defined, as percentage by weight, by the following formula:

[1−(hourly weight of ethanol at the outlet/hourly weight of ethanol at the inlet)]×100.

The hourly weight of ethanol at the inlet or at the outlet corresponds to the flow rate by weight at the inlet or at the outlet of the multitubular reactor, and can be determined conventionally, for example by gas chromatography.

During the dehydrogenation stage, the transformation of the feedstock may be accompanied by a deactivation of the dehydrogenation catalyst, for example by coking, by adsorption of inhibitor compounds and/or by sintering. The dehydrogenation catalyst can thus advantageously be periodically subjected to a regeneration or a replacement. Thus, in a particular embodiment of the invention, the process comprises a regeneration-replacement stage. In this particular embodiment, the reaction section preferably comprises at least two multitubular reactors. Preferably, the multitubular reactors are used in an alternating mode, also called swing mode, in order to alternate the reaction (or operating) phases and the phases of regeneration and/or replacement of said dehydrogenation catalyst. The objective of the regeneration is to incinerate the organic deposits as well as the entities containing nitrogen and sulfur, contained at the surface and within said dehydrogenation catalyst. The replacement makes it possible to replace the spent catalyst, that is to say catalyst which has been used during at least one dehydrogenation stage, with fresh dehydrogenation catalyst, that is to say catalyst which has not yet been used.

The regeneration of the dehydrogenation catalyst can advantageously be carried out by oxidation of the coke and of the inhibitor compounds under a flow of air or under an air/nitrogen mixture, for example by using recirculation of the combustion air, with or without water, in order to dilute the oxygen and to control the regeneration exotherm. In this case, the oxygen content is advantageously adjusted at the inlet of the reactor by a contribution of air. The regeneration preferably takes place at a pressure of between atmospheric pressure and the reaction pressure.

According to a very particular embodiment of the invention, the regeneration-replacement stage comprises:

the replacement of the dehydrogenation catalyst, in particular the replacement of the spent catalyst, with fresh catalyst, preferably comprising at least the element copper on an inorganic support, preferentially silica, or the regeneration of the dehydrogenation catalyst, preferably comprising at least three phases, with at least a first phase of flushing with nitrogen at a temperature preferably of between 200 and 350° C., preferably between 250 and 300° C., at least a second phase of flushing with a gas comprising oxygen, preferably comprising nitrogen and oxygen, at a temperature of between 300 and 650° C., preferably between 350° C. and 600° C., advantageously until there is no longer consumption of oxygen, a sign of complete combustion of the coke, and at least a third phase of flushing with nitrogen at a temperature preferably of between 200 and 350° C. The regeneration can optionally comprise, in addition, a phase of redispersion of the active phase, preferably comprising at least the element copper and optionally the element chromium, over the inorganic support, preferably silica.

Very advantageously, the dehydrogenation effluent obtained on conclusion of the reaction section of the dehydrogenation stage, which comprises at least acetaldehyde, hydrogen, optionally water and unconverted ethanol, can be sent to a separation section in order to optionally separate, at least in part, the hydrogen generated during the dehydrogenation reaction.

The dehydrogenation effluent obtained on conclusion of the reaction section, or the effluent obtained on conclusion of the separation section, can also be subjected, either directly or indirectly, to a treatment so as to separate a flow comprising the unconverted ethanol, it then being possible for said unconverted ethanol flow to be recycled to the reaction section in order to feed the multitubular reactor(s) optionally as a mixture with the feedstock.

Advantageously, the dehydrogenation process according to the invention can be integrated as a reaction stage into a more general process for the conversion of ethanol. In particular, the dehydrogenation process according to the invention can be integrated into a process for the production of butadiene from ethanol, as first reaction stage for conversion of ethanol into acetaldehyde, and is advantageously followed by a second reaction stage of conversion of an ethanol-acetaldehyde mixture into butadiene. Such a process for the production of butadiene from ethanol, in two reaction stages, can, for example, be the process described in the patent FR 3 026 100. More particularly, stage A) of the process described in the patent FR 3 026 100 is replaced by the dehydrogenation process described above in this description, stages B), C1), D1), D2), D3), E1), E2), and the optional stages C2), D2bis), F), of the process described in the patent FR 3 026 100 remaining identical.

Thus, the present invention additionally relates to a process for the production of butadiene from an ethanol feedstock comprising at least 80% by weight of ethanol, comprising at least:

A) a stage of conversion of ethanol into acetaldehyde employing the process for the dehydrogenation of ethanol described above, in which said feedstock which feeds the tubes of the multitubular reactor is at least in part a fraction of an ethanol-rich effluent, advantageously resulting from stage E1), in order to produce a dehydrogenation effluent, and optionally a separation section in order to treat the dehydrogenation effluent and to separate at least a hydrogen effluent in gaseous form and an ethanol/acetaldehyde effluent in liquid form;

B) a stage for conversion into butadiene comprising at least a reaction section B fed at least with a fraction or all of said dehydrogenation effluent resulting from stage A), or optional ethanol/acetaldehyde effluent resulting from the optional separation section of stage A), optionally with a liquid ethanol-rich effluent advantageously resulting from the optional stage C1), with a fraction or all of an acetaldehyde-rich effluent advantageously resulting from stage E1), operated in the presence of a catalyst, preferably comprising the element tantalum and an inorganic support preferably comprising silica, at a temperature of between 300° C. and 400° C., preferably between 320° C. and 370° C., and at a pressure of between 0.1 and 1.0 MPa, preferably between 0.1 and 0.5 MPa, in a preferred way between 0.1 and 0.3 MPa, the feed flow rates being adjusted so that the molar ratio of the ethanol, with respect to the acetaldehyde, at the inlet of said reaction section is between 1 and 5, preferably between 1 and 3.5, in a preferred way between 2 and 3 and in a very preferred way between 2.4 and 2.7, and a separation section in order to treat the effluent from said reaction section B and to separate at least a gaseous effluent and a liquid effluent;

C1) optionally a stage of treatment of the hydrogen comprising at least a compression section compressing said hydrogen effluent resulting from stage A) to a pressure of between 0.1 and 1.0 MPa, advantageously between 0.1 and 0.7 MPa, in a preferred way between 0.4 and 0.68 MPa, and a gas-liquid scrubbing section fed at a temperature of between 15° C. and –30° C., preferably between 0° C. and –15° C., with a fraction of said ethanol-rich effluent advantageously resulting from stage E1) and with a fraction of said ethanol/acetaldehyde effluent resulting from stage A), and fed at a temperature of between 25° C. and 60° C., preferentially between 30° C. and 40° C., with said compressed hydrogen effluent, and producing at least a liquid ethanol-rich effluent and a purified hydrogen effluent;

D1) a stage of extraction of the butadiene comprising at least:

(i) a compression section compressing said gaseous effluent resulting from stage B) to a pressure of between 0.1 and 1.0 MPa, preferably between 0.1 and 0.7 MPa, in a preferred way between 0, 2 and 0.5 MPa, optionally said compressed gaseous effluent resulting from stage B) subsequently being cooled to a temperature between 25° C. and 60° C., preferentially between 30° C. and 40° C., (ii) a gas-liquid scrubbing section comprising a scrubbing column fed, at the top, at a temperature of between 20 and –20° C., preferentially between 15° C. and 5° C., with an ethanol flow consisting of the ethanol feedstock of the process and optionally of a fraction of the ethanol-rich effluent advantageously resulting from stage E1) and, at the bottom, with said gaseous effluent resulting from stage B) compressed in section i) and optionally cooled, producing at least a liquid scrubbing effluent and a gaseous by-products effluent, and (iii) a distillation section operated at a pressure of between 0.1 and 1 MPa, in a preferred way between 0.2 and 0.5 MPa, fed at least with the liquid effluent resulting from said stage B) and with the liquid effluent from said gas-liquid scrubbing section, producing at least a crude butadiene effluent and an ethanol/acetaldehyde/water effluent;

D2) a stage of first purification of the butadiene comprising at least a gas-liquid scrubbing section fed at the bottom with the crude butadiene effluent resulting from D1) and at the top with a flow of water which can be a flow of water of origin external to said process for the production of butadiene and/or a fraction of the aqueous effluent advantageously resulting from stage E1), said water flow preferably being cooled prior to the gas-liquid scrubbing section to a temperature of less than 25° C., preferably of less than 20° C., said gas-liquid scrubbing section being advantageously operated at a pressure of between 0.1 and 1 MPa, said gas-liquid scrubbing section producing a pre-purified butadiene effluent at the top and a waste water effluent at the bottom;

D3) a subsequent stage of purification of the butadiene, fed at least with said pre-purified butadiene effluent resulting from said stage D2), and producing at least a purified butadiene effluent, said subsequent purification stage advantageously employing a section for drying said pre-purified butadiene effluent resulting from said stage D2), preferably in the presence of at least one adsorbent, then at least a cryogenic distillation section or at least a distillation and extractive distillation section;

E2) a stage of removal of impurities and brown oils, fed at least with the ethanol/acetaldehyde/water effluent resulting from stage D1) and with at least a fraction of a water-rich effluent advantageously resulting from stage E1), and producing at least a water/ethanol/acetaldehyde raffinate, a light brown oils effluent and a heavy brown oils effluent, said stage of removal of impurities and brown oils preferably employing at least:

E2i) a scrubbing/backscrubbing section operated at a pressure between 0.1 and 0.5 MPa, preferentially between 0.2 and 0.4 MPa, and fed with the ethanol/acetaldehyde/water effluent resulting from stage D1) and preferentially at the bottom with a hydrocarbon effluent and at the top with at least a fraction of the water-rich effluent advantageously resulting from stage E1), said hydrocarbon and water-rich effluents preferably being at a temperature between 10 and 70° C., preferentially between 45 and 55° C., and producing said water/ethanol/acetaldehyde raffinate and a hydrocarbon extract, E2ii) a section for the distillation of the light brown oils which is fed with the hydrocarbon extract and which produces said light brown oils effluent and a hydrocarbon residue, and E2iii) a section for the distillation of the heavy brown oils fed with the hydrocarbon residue and producing said heavy brown oils effluent and a hydrocarbon distillate, which advantageously composes, at least in part, the hydrocarbon effluent from the scrubbing/backscrubbing section;

E1) a stage of treatment of the effluents which is fed at least with a water/ethanol/acetaldehyde raffinate advantageously resulting from stage E2), preferably employing at least two distillation sections, in particular at least a section for distillation of the acetaldehyde and at least a section for distillation of the water and the ethanol, and said stage of treatment of the effluents producing at least an ethanol-rich effluent, preferably comprising at least 80% by weight of ethanol, an acetaldehyde-rich effluent, preferably comprising at least 80% by weight of acetaldehyde, and a water-rich effluent, preferably comprising at least 80% by weight of water.

In this particular embodiment of the invention, the ethanol-rich effluent obtained in stage E1 and recycled as feedstock of stage A) during which the dehydrogenation of the ethanol is carried out can conventionally comprise up to 18% by weight of water.

Thus, the dehydrogenation process according to the invention appears to be particularly advantageous in this butadiene production process insofar as the ethanol-rich effluent, feeding the dehydrogenation reaction section, conventionally comprising up to 18% by weight of water, does not make it possible to envisage an addition of steam as thermal diluent to the feedstock of the dehydrogenation stage without early deactivation of the dehydrogenation catalyst, the performance qualities of which are generally reduced when the feedstocks comprise 20% by weight or more of water.

The following examples illustrate the invention without limiting the scope thereof.

EXAMPLES

Example 1: In Accordance with the Invention

Example 1 illustrates a dehydrogenation process according to the invention.

The feedstock to be treated comprises 82% by weight of ethanol and 18% by weight of water. The dehydrogenation reaction is carried out in a multitubular reactor made of alloy steel, the tubes of which comprise a fixed bed of Octolyst® 2001 catalyst sold by Evonik. The feedstock is introduced into the tubes in gaseous form, simultaneously. The heat-transfer fluid used is Dowtherm™ A oil from Dow, and is introduced into the shell in gaseous form, in particular in saturated vapor form.

All of the parameters of the reactor and of the operating conditions used are summarized in Table 1.

TABLE 1

| Parameters (unit) | Value |
|---|---|
| Number of tubes (—) | 5312 |
| Height of the tubes (m) | 2.5 |
| Internal diameter of the tubes (mm) | 45.2 |
| Thickness of the wall of the tubes (mm) | 2.77 |
| Weight of catalyst (kg) | 15 670 |
| Mean equivalent diameter of the catalyst particles (mm) | 4 |
| Inlet temperature of the feedstock (° C.) | 270 |
| Inlet pressure of the feedstock (MPa) | 0.35 |
| Flow rate of the feedstock (kg/h) | 78 346 |
| WWH (h$^{-1}$) feedstock, total | 5 |
| Temperature of the oil at the inlet of the shell (° C.) | 290 |
| Pressure of the oil at the inlet of the shell (MPa) | 0.198 |
| Flow rate of the oil at the shell inlet (kg/h) | 120 000 |
| Ratio of the flow rates by weight of the oil to the feedstock | Approximately 1.53 |

The dehydrogenation effluent is recovered at the reactor outlet at a flow rate of 78 346 kg/h, a temperature of approximately 277° C. and a pressure of approximately 0.29 MPa (i.e. a drop in pressure of approximately 0.6 bar, that is to say approximately 0.06 MPa). At the shell outlet, a gas-Dowtherm™ A oil liquid mixture, at 290° C., is recovered.

The dehydrogenation effluent obtained is analyzed by gas chromatography. It exhibits the following composition:

57% by weight of ethanol,

22% by weight of acetaldehyde,

18% by weight of water,

2% by weight of other compounds, and in particular: ethyl acetate, acetic acid and butanol, approximately 1% by weight of hydrogen.

The performance qualities of the process which are obtained are satisfactory since the process makes it possible to achieve a conversion of 35% by weight of the ethanol with a selectivity for acetaldehyde of 92%.

Example 2: Not in Accordance with the Invention

Example 2 illustrates a process implementing the dehydrogenation reaction in adiabatic reactors.

The same feedstock as that of example 1 is treated by the process of example 2: it comprises 18% by weight of water and 82% by weight of ethanol.

The same Octolyst® 2001 catalyst from Evonik is used as dehydrogenation catalyst.

The dehydrogenation reaction is carried out in a sequence of 11 axial adiabatic reactors in series, each comprising a fixed bed of dehydrogenation catalyst (Octolyst® 2001) and between which heat exchangers are inserted in order to heat the liquid flow between each bed. The reaction unit thus comprises 11 adiabatic reactors in series and 10 heat exchangers.

The feedstock, which comprises 82% by weight of ethanol and 18% by weight of water, is introduced into the first reactor at an inlet temperature of 275° C., at an inlet pressure of 0.57 MPa and at a flow rate of 78 346 kg/h, corresponding to a WWH of 2 h$^{-1}$ with respect to the ethanol.

The parameters of the adiabatic reactors having axial fixed beds, the operating conditions and the degrees of conversion of the ethanol which are obtained are presented in table 2. The outlet pressure of the eleventh reactor is 0.25 MPa.

TABLE 2

| | Reactor No. | | | | | | | | | | |
|---|---|---|---|---|---|---|---|---|---|---|---|
| | 1 | 2 | 3 | 4 | 5 | 6 | 7 | 8 | 9 | 10 | 11 |
| Volume of the catalytic bed (m$^3$) | 1.7 | 3.3 | 4.2 | 4.2 | 4.2 | 4.2 | 4.2 | 4.2 | 4.2 | 4.2 | 4.2 |
| Cumulative volume (m$^3$) | 1.7 | 5.0 | 9.2 | 13.4 | 17.6 | 21.8 | 26.0 | 30.2 | 34.4 | 38.6 | 42.8 |
| T$_{inlet}$ (° C.) | 275 | 275 | 275 | 275 | 275 | 275 | 275 | 275 | 275 | 275 | 275 |
| T$_{outlet}$ (° C.) | 233 | 244 | 253 | 259 | 262 | 265 | 267 | 267 | 267 | 267 | 267 |
| Conversion (%) | 8 | 14 | 18 | 21 | 24 | 26 | 28 | 29 | 31 | 33 | 34 |

At the outlet of the reaction unit, a conversion of ethanol of 34% is achieved and the selectivity for acetaldehyde is 92%.

Example 3: Not in Accordance with the Invention

Example 3 illustrates a process implementing the dehydrogenation reaction in adiabatic reactors in the presence of a thermal diluent.

The same Octolyst® 2001 catalyst from Evonik as that used in the processes described in example 1 and example 2 is used as dehydrogenation catalyst.

The feedstock which is treated by the process of example 3 is for its part diluted with steam to a dilution of 60% by weight of water per 40% by weight of ethanol. This feedstock is introduced into a series of radial adiabatic reactors each comprising a fixed bed of dehydrogenation catalyst and between which heat exchangers are inserted in order to heat the liquid flow between each bed. The feedstock, which comprises 40% by weight of ethanol and 60% by weight of water, is introduced into the first reactor at an inlet temperature of 275° C., at an inlet pressure of 0.37 MPa and at a flow rate of 78 346 kg/h.

The parameters of the adiabatic reactors having radial fixed beds, the operating conditions and the degrees of conversion of the ethanol which are obtained are presented in table 3. The outlet pressure of the reactor No. 4 is 0.20 MPa.

TABLE 3

|  | Reactor No. | | | |
| --- | --- | --- | --- | --- |
|  | 1 | 2 | 3 | 4 |
| Volume of the catalytic bed (m³) | 1.7 | 3.3 | 4.2 | 4.2 |
| Cumulative volume (m³) | 1.7 | 5.0 | 9.2 | 13.4 |
| $T_{inlet}$ (° C.) | 275 | 275 | 275 | 275 |
| $T_{outlet}$ (° C.) | 225 | 254 | 255 | 260 |
| Conversion (%) | 16 | 23 | 30 | 35 |

A dilution of the ethanol of 60% by weight with steam makes it possible to achieve a conversion of the ethanol of 35% after only 4 adiabatic reactors.

However, under the conditions of the process of example 3 and in particular with an ethanol feedstock diluted to 60% by weight of water, a deactivation of the dehydrogenation catalyst which is faster than in the process of example 2 is observed.

The invention claimed is:

1. A process for the dehydrogenation of ethanol to give acetaldehyde, comprising:

a stage of dehydrogenation of a feedstock comprising ethanol, said dehydrogenation stage employing a reaction section comprising at least one reactor which comprises one or a plurality of tubes and a shell, said tube(s) each comprising at least one fixed bed of at least one dehydrogenation catalyst, said feedstock feeding said tube(s) in gaseous form, at an inlet temperature of said feedstock of greater than or equal to 240° C., at an inlet pressure of said feedstock of between 0.1 and 1.0 MPa, and at a weight hourly space velocity (WWH) of the feedstock at the inlet of between 2 and 15 h⁻¹, a heat-transfer fluid circulating in said shell so that said heat-transfer fluid is introduced into said shell in gaseous form and is, at the shell outlet, at least partly in liquid form, said heat-transfer fluid being introduced into the shell at a flow rate such that the ratio of the flow rate by weight of said heat-transfer fluid at the shell inlet, with respect to the flow rate by weight of said feedstock at the inlet of the tube(s), is greater than or equal to 1.0, said heat-transfer fluid being introduced into the shell at an inlet temperature of the heat-transfer fluid of greater than or equal to 260° C. and less than or equal to 400° C., and at an inlet pressure of the heat-transfer fluid of greater than or equal to 0.10 MPa and less than or equal to 1.10 MPa, and said process producing a dehydrogenation effluent comprising at least acetaldehyde, hydrogen and unconverted ethanol.

2. The process as claimed in claim 1, wherein the heat-transfer fluid is an oil comprising a eutectic mixture of organic compounds having saturated vapor pressures such that the difference between the saturated vapor pressures of the organic compounds of the oil, at a given temperature, is less than or equal to 50 Pa less than or equal to 20 Pa, in a preferred way less than or equal to 10 Pa.

3. The process as claimed in claim 1, wherein the feedstock comprises at least 50% by weight of ethanol and optionally water.

4. The process as claimed in claim 1, wherein said at least one reactor comprises a plurality of tubes.

5. The process as claimed in claim 1, wherein the tube(s) of the reactor has (have) a length of between 1 and 6 m.

6. The process as claimed in claim 1, wherein the tube(s) of the reactor exhibit(s) an internal diameter between 30.0 and 60.0 mm; and a tube wall thickness between 1.5 and 5.0 mm.

7. The process as claimed in claim 1, wherein the dehydrogenation catalyst comprises at least the element copper on silica support.

8. The process as claimed in claim 1, wherein the dehydrogenation catalyst is in the form of particles with a mean equivalent diameter between 0.5 and 10.0 mm.

9. The process as claimed in claim 1, wherein the inlet temperature of the feedstock in the tube(s) is between 240° C. and 350° C.

10. The process as claimed in claim 1, wherein the inlet pressure of the feedstock in the tube(s) is between 0.2 and 0.5 MPa.

11. The process as claimed in claim 1, wherein the weight hourly space velocity (WWH) of the feedstock at the inlet of the reactor is between 2 and 10 h⁻¹.

12. The process as claimed in claim 1, wherein the heat-transfer fluid is introduced into the shell of the reactor at a flow rate such that the ratio of the flow rate by weight of said heat-transfer fluid at the shell inlet, with respect to the flow rate by weight of said feedstock at the inlet of the tube(s), is greater than or equal to 1.5 and less than or equal to 10.0.

13. The process as claimed in claim 1, wherein the heat-transfer fluid is introduced into the shell of the reactor at an inlet temperature of greater than or equal to 260° C. and less than or equal to 400° C., and at an inlet pressure of the heat-transfer fluid of greater than or equal to 0.10 MPa and less than or equal to 1.10 MPa.

14. The process as claimed in claim 1, further comprising a stage of conditioning of the heat-transfer fluid comprising a substage of recovery of the liquid heat-transfer fluid at the shell outlet of the reactor of the dehydrogenation stage and a stage of compression and/or heating of the heat-transfer fluid in order to obtain a heat-transfer fluid in gaseous form at the inlet temperature and pressure of the heat-transfer fluid in the shell of the dehydrogenation stage.

15. A process for the production of butadiene from an ethanol feedstock comprising at least 80% by weight of ethanol, comprising:

A) a stage of conversion of ethanol into acetaldehyde employing the process for the dehydrogenation of ethanol as claimed in claim 1, wherein said feedstock which feeds the tubes of the reactor is at least in part a fraction of an ethanol-rich effluent, advantageously resulting from stage E1), in order to produce a dehydrogenation effluent, and optionally a separation section in order to treat the dehydrogenation effluent and to separate at least a hydrogen effluent in gaseous form and an ethanol/acetaldehyde effluent in liquid form;

B) a stage for conversion into butadiene comprising at least a reaction section B fed at least with a fraction or all of said dehydrogenation effluent resulting from stage A), or optional ethanol/acetaldehyde effluent resulting from the optional separation section of stage A), optionally with a liquid ethanol-rich effluent resulting from stage C1), with a fraction or all of an acetaldehyde-rich effluent resulting from stage E1), operated in the presence of a catalyst comprising the element tantalum and an inorganic support, at a temperature of between 300° C. and 400° C. and at a pressure of between 0.1 and 1.0 MPa, the feed flow rates being adjusted so that the molar ratio of the ethanol, with respect to the acetaldehyde, at the inlet of said reaction section is between 1 and 5, and a separation section in order to treat the effluent from said reaction section B and to separate at least a gaseous effluent and a liquid effluent;

C1) optionally a stage of treatment of the hydrogen comprising at least a compression section compressing said hydrogen effluent resulting from stage A) to a pressure of between 0.1 and 1.0 MPa and a gas-liquid scrubbing section fed at a temperature of between 15° C. and −30° C. with a fraction of said ethanol-rich effluent and with a fraction of said ethanol/acetaldehyde effluent resulting from stage A) and fed at a temperature of between 25° C. and 60° C. with said compressed hydrogen effluent, and producing at least a liquid ethanol-rich effluent and a purified hydrogen effluent;

D1) a stage of extraction of the butadiene comprising at least:

(i) a compression section compressing said gaseous effluent resulting from stage B) to a pressure of between 0.1 and 1.0 MPa, optionally said compressed gaseous effluent resulting from stage B) subsequently being cooled to a temperature between 25° C. and 60° C., (ii) a gas-liquid scrubbing section comprising a scrubbing column fed, at the top, at a temperature of between 20 and −20° C., with an ethanol flow consisting of the ethanol feedstock of the process and optionally of a fraction of the ethanol-rich effluent and, at the bottom, with said gaseous effluent resulting from stage B) compressed and optionally cooled, producing at least a liquid scrubbing effluent and a gaseous by-products effluent, and (iii) a distillation section operated at a pressure of between 0.1 and 1 MPa, fed at least with the liquid effluent resulting from said stage B) and with the liquid effluent from said gas-liquid scrubbing section, producing at least a crude butadiene effluent and an ethanol/acetaldehyde/water effluent;

D2) a stage of first purification of the butadiene comprising at least a gas-liquid scrubbing section fed at the bottom with the crude butadiene effluent resulting from D1) and at the top with a flow of water which is a flow of water of origin external to said process for the production of butadiene and/or a fraction of the aqueous effluent resulting from stage E1), said scrubbing section producing a pre-purified butadiene effluent at the top and a waste water effluent at the bottom;

D3) a subsequent stage of purification of the butadiene, fed at least with said pre-purified butadiene effluent resulting from said stage D2) and producing at least a purified butadiene effluent;

E2) a stage of removal of impurities and brown oils, fed at least with the ethanol/acetaldehyde/water effluent resulting from stage D1) and with at least a fraction of a water-rich effluent resulting from stage E1), and producing at least a water/ethanol/acetaldehyde raffinate, a light brown oils effluent and a heavy brown oils effluent; and E1) a stage of treatment of the effluents which is fed at least with a water/ethanol/acetaldehyde raffinate resulting from stage E2), and producing at least an ethanol-rich effluent, an acetaldehyde-rich effluent and a water-rich effluent.

16. The process as claimed in claim 1, wherein the heat-transfer fluid is an oil comprising a eutectic mixture of organic compounds having saturated vapor pressures such that the difference between the saturated vapor pressures of the organic compounds of the oil, at a given temperature, is less than or equal to 20 Pa.

17. The process as claimed in claim 1, wherein the heat-transfer fluid is an oil comprising a eutectic mixture of organic compounds having saturated vapor pressures such that the difference between the saturated vapor pressures of the organic compounds of the oil, at a given temperature, is less than or equal to 10 Pa.

18. The process as claimed in claim 1, wherein the feedstock comprises at least 80% by weight of ethanol.

19. The process as claimed in claim 3, wherein the feedstock comprises less than 50% by weight water.

20. The process as claimed in claim 3, wherein the feedstock comprises less than 20% by weight water.

21. The process as claimed in claim 4, wherein said at least one reactor comprises at least 1,000 tubes and less than 20,000 tubes.

22. The process as claimed in claim 1, wherein the tube(s) of the reactor has (have) a length of between 2 and 3 m.

23. The process as claimed in claim 1, wherein the tube(s) of the reactor exhibit(s) an internal diameter between 40.0 and 50.0 mm, and a tube wall thickness between 2.0 and 4.0 mm.

24. The process as claimed in claim 23, wherein the tube(s) of the reactor exhibit(s) a tube wall thickness between 2.2 and 3.2 mm.

25. The process as claimed in claim 1, wherein the inlet temperature of the feedstock in the tube(s) is between 260° C. and 290° C.

26. The process as claimed in claim 12, in which the heat-transfer fluid is introduced into the shell of the reactor at a flow rate such that the ratio of the flow rate by weight of said heat-transfer fluid at the shell inlet, with respect to the flow rate by weight of said feedstock at the inlet of the tube(s), is less than or equal to 5.0.

27. The process as claimed in claim 1, in which the heat-transfer fluid is introduced into the shell of the reactor at an inlet temperature of greater than or equal to 290° C. and less than or equal to 380° C. and at an inlet pressure of the heat-transfer fluid of greater than or equal to 0.13 MPa and less than or equal to 0.85 MPa.

* * * * *